(12) United States Patent
Buchstaller (10) Patent No.: US 11,013,227 B2
(45) Date of Patent: May 25, 2021

(54) DEVICE FOR HOLDING A BAIT (71) Applicant: Jürgen Buchstaller, Nuremberg (DE)

(72) Inventor: Jürgen Buchstaller, Nuremberg (DE)

( * ) Notice: Subject to any disclaimer, the term of this patent is extended or adjusted under 35 U.S.C. 154(b) by 195 days.

(21) Appl. No.: 16/303,110

(22) PCT Filed: May 29, 2017

(86) PCT No.: PCT/EP2017/062874
§ 371 (c)(1),
(2) Date: Nov. 19, 2018

(87) PCT Pub. No.: WO2017/207479
PCT Pub. Date: Dec. 7, 2017

(65) Prior Publication Data
US 2020/0315157 A1     Oct. 8, 2020

(30) Foreign Application Priority Data

May 30, 2016   (DE) .......................... 102016109930.9

(51) Int. Cl.
*A01M 31/00* (2006.01)
*G01V 9/00* (2006.01)
*G01N 33/00* (2006.01)
*G01G 19/00* (2006.01)

(52) U.S. Cl.
CPC ........... *A01M 31/002* (2013.01); *G01G 19/00* (2013.01); *G01N 33/004* (2013.01); *G01V 9/005* (2013.01)

(58) Field of Classification Search
None
See application file for complete search history.

(56) References Cited

U.S. PATENT DOCUMENTS

| | | | | |
|---|---|---|---|---|
| 7,051,472 | B1* | 5/2006 | Kelly | A01M 1/023 43/58 |
| 8,839,550 | B2* | 9/2014 | Gardner | A01M 23/16 43/61 |
| 9,015,987 | B2* | 4/2015 | Moran | G01C 15/00 43/61 |
| 9,179,665 | B2* | 11/2015 | Frojmovics | A01M 31/002 |
| 9,351,483 | B2* | 5/2016 | Fritzboger | A01M 23/36 |
| 9,439,412 | B2* | 9/2016 | Kittelson | A01M 23/18 |
| 10,111,416 | B2* | 10/2018 | Rich | A01M 31/002 |
| 10,455,828 | B2* | 10/2019 | Jensen | A01M 23/24 |

(Continued)

FOREIGN PATENT DOCUMENTS

| | | |
|---|---|---|
| DE | 202015008952 U1 | 5/2016 |
| EP | 2775447 A1 | 9/2014 |
| WO | 2015179899 A1 | 12/2015 |

OTHER PUBLICATIONS

Hans-Joachim Pelz, "Wenn das Rattengift nicht mehr wirkt", Top AGRAR, vol. 1/2007, Jan. 31, 2007, pp. S14-S17, XP055406050.

*Primary Examiner* — Chico A Foxx
(74) *Attorney, Agent, or Firm* — Rimôn, P.C.

(57) ABSTRACT

The invention relates to an apparatus 1 for holding a piece of bait 2, in particular a piece of bait 2 for pests 14, preferably for rodents, comprising:
  a housing part 3 which has a receiving space 6 for receiving a piece of bait 2 and can be inserted into a part of a sewer system,
  a detecting device 9, equipped to detect a first item of information,
  an output device 11, equipped to output a first item of information detected by the detecting device 9.

15 Claims, 4 Drawing Sheets

(56) References Cited

U.S. PATENT DOCUMENTS

| | | | | |
|---|---|---|---|---|
| 2002/0124458 A1* | 9/2002 | Clark | ............... | A01M 1/2011 |
| | | | | 43/124 |
| 2005/0151653 A1* | 7/2005 | Chan | ............... | A01M 31/002 |
| | | | | 340/573.2 |
| 2006/0123693 A1* | 6/2006 | Muller | ............... | A01M 23/38 |
| | | | | 43/99 |
| 2011/0056117 A1* | 3/2011 | Fritzboger | ............ | A01M 27/00 |
| | | | | 43/73 |
| 2014/0279600 A1* | 9/2014 | Chait | ............... | G06Q 30/018 |
| | | | | 705/317 |
| 2017/0055516 A1* | 3/2017 | Bittlinger | ............... | E02D 29/12 |
| 2017/0318796 A1* | 11/2017 | Vaisblat | ............ | A01M 25/004 |
| 2017/0360024 A1* | 12/2017 | Bittlinger | ............ | A01M 25/002 |
| 2018/0007889 A1* | 1/2018 | Bittlinger | ............ | A01M 25/004 |
| 2018/0132475 A1* | 5/2018 | Bittlinger | ............ | A01M 1/2011 |
| 2018/0199565 A1* | 7/2018 | Zosimadis | ............ | A01M 23/18 |
| 2018/0325092 A1* | 11/2018 | Round | ............... | A01M 23/12 |
| 2019/0166821 A1* | 6/2019 | Fritzboger | ............ | A01M 23/24 |

\* cited by examiner

DEVICE FOR HOLDING A BAIT

CROSS-REFERENCE TO RELATED APPLICATIONS

This application is a U.S. national stage entry under 35 U.S.C. § 371 of International Application Ser. No. PCT/EP2017/062874 filed May 29, 2017, which claims priority to German Patent Application serial no. 102016109930.9 filed May 30, 2016. The contents of these applications are incorporated herein by reference in their entirety.

The invention relates to an apparatus for holding bait, in particular bait for pests, preferably for rodents.

Such apparatuses are used for holding bait, e.g., for pests such as rodents, insects, etc., and are fundamentally known in a variety of different embodiments. These apparatuses are typically used for the purpose of pest control. The bait held by the apparatus contains substances accordingly, which are optionally toxic and cause the death of the pests and/or prevent the pests from reproducing.

The scope of function of corresponding apparatuses is limited so far essentially to reliable holding of bait.

There is a demand for expanding the scope of function of corresponding apparatuses, in particular with regard to the possibility of detecting specific data and/or information, optionally bait-specific and/or pest-specific data and/or information, the evaluation and output thereof to an output and/or communications partner, i.e., a user, for example.

The invention is based on the object of providing an apparatus for holding bait, the functional scope of which has been expanded.

This object is achieved by an apparatus for holding bait according to the claims. The dependent claims relate to possible embodiments of the apparatus. This object is also achieved by a transmission system according to the claims and related methods.

The apparatus described herein is used for holding at least one piece of bait, in particular at least one piece of bait for pests, preferably for rodents, insects, etc. The bait typically contains substances which are optionally toxic and cause the death of the pests and/or prevent the pests from reproducing. This apparatus may also be referred to as a bait-holding apparatus.

The apparatus comprises a housing part. The housing part may be arranged above ground and/or below ground. In particular the housing part may be releasably attached to third objects above and/or below ground by means of suitable fastening devices, in particular on the housing part, in particular being releasably attachable (without damage or destruction). The housing part in particular can be inserted into a shaft mine and/or a sewer system and/or into a part of such a system. A part of a corresponding shaft mine and/or sewer system may be considered as an example of a third object, as mentioned above.

The housing part comprises at least one receiving space and/or interior space. Suitable holding options for holding at least one piece of bait are arranged or designed in the receiving space. Corresponding holding options may be hanging devices, for example, which allow hanging storage of bait (in the receiving space), or platform devices (bait platforms), which allow horizontal or vertical storage of bait (in the receiving space). There may of course be various holding options for holding at least one piece of bait, i.e., in particular (various) hanging devices and/or (various) platform devices.

If a corresponding platform device is present, it is typically provided with at least one passage, through which a pest can move from an area (of the housing part) beneath the platform device to an area (of the housing part) situated above the platform device or vice versa. The bait is typically in the area (of the housing part) situated above the platform device.

The apparatus additionally comprises at least one detecting device. The detecting device is equipped for detecting a first item of information. The first item of information relates to data that can be output via an output device configured with appropriate hardware and/or software or can be processed further via a control unit configured with appropriate hardware and/or software. Specific examples of first items of information are given further below. To detect first items of information, the detecting device is equipped with suitable detecting elements. Examples of detecting elements are also given further below.

The apparatus additionally comprises at least one output device. The output device is directly or indirectly connected to and/or communicates with the detecting device via data link. The output device is equipped for output of first items of information detected by the detecting device. First items of information detected by the detecting device can then be output directly via the output device, i.e., without data processing.

The apparatus may additionally comprise at least one control unit. The control unit is directly or indirectly connected to and/or communicates with the detecting device via a data link, i.e., with at least one data transmission element in between. The control unit is equipped to generate a second item of information on the basis of a first item of information detected by the detecting device. The second item of information is data derived from the first item of information by data processing and can also be output by an output device configured with appropriate hardware and/or software. The information content of the second item of information typically differs from the information content of the first item of information due to further data processing. Specific examples of the second item of information are given further below. To generate a second item of information, the control unit is equipped with suitable hardware and/or software elements; in other words, the control unit is configured with regard to the hardware and/or software for further processing of the data detected by the detecting device.

If there is a corresponding control unit, the output device may be directly or indirectly connected to and/or communicate with at least the control unit via data link. The output device is also equipped for output of second items of information generated by means of the control unit.

It can be derived from the preceding statements that first items of information, which is typically not raw data that has been prepared and/or (pre)processed by data processing and/or second item of information, which is typically not prepared and/or (pre)processed data, can be output via the output device. This means that there may but need not be data preparation and/or (pre)processing of the first items of information at the apparatus end.

Output of a first and/or second item of information may be understood to be actual and/or direct output of the first and/or second items information to and/or via an output device. A user can actually and/or directly (physically) perceive the first and/or second items of information output on the output device. An output device may be designed accordingly as a signal output device for direct output of signals describing first and/or second items of information to at least one user. The first and/or second items of information may be output via acoustic and/or haptic and/or optical signals, for example.

A signal output device may be an acoustic signal output device, i.e., a loudspeaker device, for example, an optical signal output device, i.e., a display device, for example, or a haptic signal device, i.e., a vibration device, for example.

However, output of first and/or second items of information may also be understood to be transmission and/or transfer of first and/or second items of information to an output and/or communications partner communicating with the output device. Accordingly, an output device may be a transmission and/or transfer device, which is designed for transmission and/or transfer of first and/or second items of generated information to at least one communications partner, in particular to a (mobile) operator device or terminal on the user end and/or to a local or global data network, for example, an intranet or the Internet ("cloud"). The transmission and/or transfer may be radio-based in particular. The transmitting device may be equipped accordingly for radio-based data transmission and/or transfer. Radio-based data transmission may be implemented via radio-based data transmission possibilities and/or standards, i.e., Bluetooth, DECT, WLAN, etc., for example. The first and/or second items of information may be output actually and/or directly here to an output and/or communications partner, to which the first and/or second items of information has/have been transmitted and/or transferred via the output device. The communications partner may therefore be equipped with suitable signal output devices, for example, acoustic and/or haptic and/or optical devices. The communications partner may be a (mobile) operating device and/or terminal at the user end, as mentioned above.

The detecting device and/or the control unit and/or the output device and/or a marking device, as explained in greater detail below, may form an integral component of the housing part. However, it is also conceivable for the detecting device and/or the control unit and/or the output device and/or the marking device, as explained in greater detail below, to form an integral component of a part that is or can be connected to the housing part or of a part that is separate from the housing part, i.e., is not or cannot be connected to the housing part in a spatial physical manner. The first type of variant permits a highly integrated design of the apparatus from a functional standpoint, while the latter variants permit the option of easy replacement of the respective devices, for example, for the purpose of service and/or repair work and/or an option of easy access to the respective devices. A part that is connectable to the housing part may be a receiving chamber, which is releasably connectable to the housing part and in which electrical and/or electronic components of the apparatus in particular the detecting device, the control unit on the output device, is or can be arranged, such device(s) offering protection of these components from external influences, i.e., in particular climate and mechanical influences.

The scope of function of the apparatus is expanded by the principle of detection of first items of information, optional generation of second items of information on the basis of first items of information detected and output of first and/or second items of information.

Examples of first and second items of information are also given below:

A first item of information may be bait information, describing and/or containing a bait parameter of a piece of bait. At least one property of a piece of bait can be described qualitatively or quantitatively by a bait parameter. The presence of bait can of course also be described qualitatively or quantitatively by a bait parameter. A bait parameter may of course also qualitatively or quantitatively describe, for example, at least one chemical and/or physical and/or geometric parameter of a piece of bait, i.e., the (chemical) composition (chemical parameter), the weight (physical parameter), the shape or volume (geometric parameter), of a piece of bait. A bait parameter may of course also qualitatively or quantitatively describe and/or include at least one parameter derived from at least one chemical and/or physical and/or geometric parameter of a piece of bait.

Alternatively, or additionally, a first item of information may be an item of pest information, which describes and/or contains at least one pest parameter of a pest. At least one property of a pest can be described qualitatively or quantitatively via a pest parameter. The presence of a pest can of course also be described qualitatively or quantitatively via a pest parameter. A pest parameter may thus qualitatively or quantitatively describe, for example, detected pests and/or movements of one or more pests detected inside and/or outside of the receiving space on the housing part end. A pest parameter may of course also qualitatively or quantitatively describe and/or include at least one parameter derived from detected pests and/or movements of one or more detected pests inside and/or outside of the receiving space on the housing part end.

A second item of information may be user information generated on the basis of bait information detected and/or pest information detected as examples of first items of information. User information is basically information directed at a user of the apparatus.

User information may describe and/or include bait dosing information and/or bait checking information and/or pest resistance information.

Bait dosing information may describe and/or include qualitative or quantitative instruction and/or recommendation directed at a user for introducing (new) bait into the receiving space on the housing part end, such instruction and/or recommendation being expedient in particular with respect to a certain target variable, in particular preventing a pest from developing resistance to certain bait. Thus, an instruction and/or recommendation about which bait, in particular which active ingredient contained in the bait, a user should expediently use (in the future) to equip the bait-holding apparatus with in order to prevent a pest from developing resistance to a certain type of bait, for example, can be given to a user via corresponding bait dosing information. It is known that pests can develop resistance after repeated administration of one and the same type of bait—the active substance contained in the bait is what is important here—such that the resistance cancels and/or negates the efficacy of the bait. This can be prevented by providing appropriate bait dosing information.

Detected bait information can provide information about the chemical composition of the bait held on the apparatus end, for example, or about the (un)changed weight and/or volume of the bait, optionally over a certain period of time. Bait dosing information is created on the basis of information about the bait, i.e., its chemical composition and/or weight and/or volume, for example, as provided by the bait information. Thus, dosing of a different type of bait may (optionally) be instructed via corresponding bait dosing information.

In an exemplary case, bait dosing information may instruct about dosing of a second type of bait, which is different from the first bait with regard to its chemical composition, based on detection and/or with information about the chemical composition of a first type of bait, for example. In another exemplary case, on the basis of detection and/or with knowledge of a weight and/or volume of a piece of bait, which varies little or not at all over a certain period of time, thereby indicating that the bait has not been accepted by the pests, bait dosing information may instruct about dosing of a second piece of bait, which is different from the first bait with regard to its chemical composition, and which is optionally accepted better by the pests.

Bait information may describe and/or include a qualitative and/or quantitative instruction for testing a type of bait that has been dosed, in particular with regard to changes in the bait attributable to a pest having taken a bite of the bait, said instruction being directed at a user and linked in particular to a certain period of time or a certain point in time. Thus, an instruction and/or recommendation may be given to a user via corresponding bait checking information about when and/or in which regular or irregular intervals of time the user should perform a check of a given piece of bait, in particular with regard to changes in the bait attributable to a pest having taken a bite of the bait. Bait typically acts within a certain period of time, after which a (definite) decline in the pest infestation is to be expected. The user may thus be given instructions about bait checking information after dosing a certain type of bait, depending on the bait-specific period of time, after which a (definite) reduction in the pest infestation is to be expected, instructing the user to check the bait held on the apparatus. Bait check information may fundamentally include a certain interval of time (checking rhythm) and/or a certain period of time and/or a certain point in time (time, day, month, year), within which and/or at which the user is to check the bait. The user may also be given check intervals at which he should perform a check of the bait.

Pest resistance information may describe and/or include current and/or future potential for development of resistance in a pest to a certain type of bait, which may have already been dosed one or more times in the past. A user may thus be given information about resistances currently and/or in the future via a corresponding pest resistance information, so that the user will vary the choice of a type of bait for equipping the bait holding apparatus accordingly, to counteract current and/or future resistances. In an exemplary case, pest resistance information may point to a resistance (developed) in the pests to a certain type of bait, namely the bait accommodated in the receiving space, based on detection of and/or information about a number of pests having remained unchanged (or increased) in the housing part over a certain period of time.

It has been pointed out that the detecting device for detecting first items of information, i.e., in particular for detecting bait information and/or pest information, is equipped with suitable detecting elements. The detecting device thus comprises at least one detecting element for detecting first items of information, i.e., in particular for detecting bait information and/or pest information.

A detecting element equipped for detecting bait information may be a sensor device for detecting a chemical and/or physical and/or geometric bait parameter. The sensor device may be equipped for detecting substances of a piece of bait, for example, optionally (highly) volatile, so that detection of a chemical bait parameter is possible. In addition, the/a (additional) sensor device may be equipped, for example, for detecting the weight of the bait, so that detection of a physical bait parameter is possible. Moreover, the/a (additional) sensor device may be equipped, for example, for detecting the shape and/or volume of a piece of bait, so that detection of a geometric bait parameter is possible.

A detecting element equipped for detecting bait information may also be a reader for readout of a memory device (memory chip, tag, etc.) containing a bait parameter, in particular on/in the bait. The reader is and/or may be in data link to the bait and/or a memory device containing a bait parameter, so that readout of the bait parameter is possible. Readout is possible when the bait is in a condition in which it is held properly by the apparatus. It is thus not absolutely necessary for a bait parameter to be detected sensorially on the apparatus end, and instead, a bait parameter can be read out by the detecting device and detected in this way.

A detecting element equipped for detecting bait information may also be a receiving device for receiving a bait parameter transmitted in particular by a user (before, during or after introducing bait into the receiving space in the housing part). The receiving device, which may form a part of an output device in the form of a transmitting device and/or transfer device on the apparatus end, is thus connected and/or connectable by data link to a transmitting device on the user end in particular, which may form a part of a (mobile) operating unit and/or terminal on the user end, so that receiving a bait parameter is possible. Thus, here again, it is not absolutely necessary to detect a bait parameter sensorially on the apparatus end, and instead, a bait parameter may be transmitted to and/or received by the detecting device and thereby detected.

A detecting element equipped for detecting information may be a sensor device for detecting pests and/or for detecting movements of pests inside and/or outside of the receiving space on the housing part. The sensor device may be equipped for detecting an atmosphere and/or a temperature inside and/or outside of the receiving space, so that detection of a pest parameter is possible. For example, detection of an atmosphere with a composition altered in comparison with a reference atmosphere (for example, an elevated $CO_2$ content) and/or detection of a temperature altered in comparison with a reference temperature may indicate the presence of pests. The sensor device comprises gas and/or temperature sensors suitable for this purpose. However, the sensor device may also be equipped to detect forces acting on a surface, i.e., a surface of a wall of the housing part and/or a surface of a platform device on the housing part, in particular compressive and/or tensile forces, so that detection of a pest parameter is possible in this way. For example, detection of a pressure or tension acting on a certain area may indicate the presence of pests. The sensor device comprises pressure and/or tension sensors suitable for this purpose.

A detecting element equipped for detecting pest information may also be a sensor device for detecting a marker device (marker) on the pest, i.e., connected externally or internally to a pest, in particular a biological, chemical, magnetic or mechanical marker. The sensor device may thus detect certain marker devices on the pest, which supply information about the presence and/or movement patterns of the pests associated therewith. Biological and/or chemical marker devices may be certain biological or chemical substances, which have been supplied to a pest externally or internally. For example, the surface of a pest may be wetted with a suitable substance. Magnetic or mechanical marker devices may be, for example, magnetic or mechanical elements which can be detected magnetically or mechanically, i.e., by means of mechanical contact, for example, and which have been supplied to a pest externally or internally. For example, a corresponding element may be attached to a body part of a pest.

For marking a pest with a corresponding marker device, the apparatus may comprise a marking device. The marking device is equipped for marking a pest with a marker device detectable by the sensor device for detecting a marker device on the pest, in particular a biological, chemical, magnetic or mechanical marker device. The marking may take place by spraying, touching a contact area, e.g., a brush type contact area, provided with a marker device, spraying, binding, gluing, stapling, etc.—depending on the structural aspects of the respective marker device.

A detecting element equipped for detecting pest information may also be a reader for readout of a memory device (memory chip, tag, etc.) containing a pest parameter, in particular on the pest. The reader device is and/or can be connected via data link to the pest and/or to a memory device containing a pest parameter, so that readout of the pest parameter is possible. Readout is possible, for example, when a pest is inside a reading area. Such a reading area may be situated inside or outside of the housing part.

A detecting element equipped for detecting pest information may also be a recording device, in particular an image and/or sound recording device, for recording pests and/or for recording movements of pests inside and/or outside of the receiving space on the housing part. The recording device may be equipped to record acoustic and/or optical information inside and/or outside of the receiving space, for example, so that detection of a pest parameter is possible. For example, a recording of a certain noise level or movement pattern may indicate the presence of pests. The recording device comprises suitable acoustic and/or optical recording elements, i.e., microphones and/or cameras, for example, for this purpose.

The detecting elements mentioned in conjunction with detection of bait information as well as pest information, in particular the aforementioned sensor devices and recording devices, may permit dynamic detection, i.e., with local and/or chronological resolution.

The apparatus may comprise a memory device (data memory). The memory device is equipped for saving first items of information detected by the detecting device, i.e., in particular bait and/or pest information, and/or for storage of second items of information generated by the control unit, i.e., in particular user information, in particular bait dosing and pest resistance information. Storage of corresponding first and second items of information is expedient from the standpoint of the described expansion of the function of the apparatus.

The apparatus may comprise a closing device, including a closing body mounted on the housing part in particular, so as to be movable relative to the housing part between an open position and a closed position. In the open position, the closing body is moved away from an access region of the housing part into the receiving space on the housing part, so that the access region is opened. In the closed position, the closing body is moved toward the access region in such a way that the access region is closed, in particular hermetically. In the closed position, contamination of the surroundings with the substances contained in the bait is prevented. The closing body may be and/or comprise a float, for example.

The invention also relates to a transmission system for transmitting first items of information, in particular bait and/or pest information, and/or second items of information, in particular user information, preferably bait dosing information and/or pest resistance information, to at least one transmission and/or communications partner. The transmission system comprises at least one apparatus, as described, and at least one transmission partner equipped to receive at least second items of information transmitted via the output device on the apparatus. The transmission partner may be in particular a (mobile) terminal and/or operating device on the user end, i.e., in particular a laptop, smartphone, tablet PC or other mobile electronic device.

The invention also relates to a method for transmitting first items of information, in particular bait and/or pest information, and/or second items of information, in particular user information, preferably bait dosing information and/or pest resistance information, to at least one transmission and/or communications partner.

In a first embodiment, the method comprises the following steps:
  detecting a first item of information, in particular bait information, describing at least one bait parameter of bait and/or pest information, describing at least one pest parameter of a pest, by the detecting device of a device as described, and
  transmitting the first detected item of information to at least one transmission partner via the output device of the apparatus.

The data processing of the first item of information can take place here outside of the device.

The method comprises the following steps of a second embodiment:
  detecting a first item of information, in particular bait information, describing at least one bait parameter of bait, and/or pest information, describing at least one pest parameter of a pest, by the detecting device of an apparatus, as described,
  generating a second item of information, in particular user information, on the basis of a first detected item of information, in particular bait information and/or detected pest information, by the control unit of the apparatus, and
  transmitting the second item of information generated to at least one transmission partner via the output device of the apparatus Data processing of the first item of information may (also) take place here inside the apparatus.

The transmission and/or communications partner, as mentioned above, may be in particular a (mobile) terminal and/or operating device on the user end, i.e., in particular a laptop, smartphone, tablet PC or other mobile electronic device.

All embodiments in conjunction with the apparatus are applicable similarly for the transmission system as well as the method and vice versa.

BRIEF DESCRIPTION OF THE FIGURES

The invention will now be explained in greater detail on the basis of exemplary embodiments in the drawings in the figures, in which.

Each figure shows a basic diagram of an apparatus 1 for holding bait 2 according to one exemplary embodiment. Individual, several or all features of the apparatuses 1 shown in the individual exemplary embodiments may be combined.

DETAILED DESCRIPTION

Apparatus 1 serves to hold bait 2, in particular at least one piece of bait 2 for pests 14, preferably for rodents, such as rats or mice, or insects such as maggots, cockroaches, etc. Bait 2 contains substances, optionally toxic, which cause pests 14 to die and/or prevent pests 14 from reproducing.

Apparatus 1 comprises a housing part 3. Housing part 3 may be arranged above ground and/or below ground. Housing part 3 is equipped with fastening devices 4, which are indicated merely schematically, and by means of which it can be fastened (releasably) onto third objects 5 above ground and/or below ground. Housing part 3 may be insertable as such into a shaft mine and/or sewer system (not shown), in particular underground, and/or into a portion of such. A portion of a corresponding shaft mine and/or sewer system may be considered as a third object 5 accordingly.

As can be seen, housing part 3 comprises a receiving space, i.e., inner space 6. A suitable holder option for holding bait 2 is arranged or formed in receiving space 6. The holding option in the exemplary embodiments shown in the figures is a platform device 7 (bait platform), which enables horizontal or vertical support of bait 2. Platform device 7 is provided with a passage 8, through which a pest 14 can move from a region of housing part 3 situated beneath platform device 7 into a region of housing part 3 situated above platform device 7 or vice versa. As can be seen, bait 2 is in the region of housing part 3 situated above platform device 7.

Although not shown in the figures, an alternative or supplementary holding option may also be a hanging device (not shown), which permits hanging support of bait 2.

Apparatus 1 additionally comprises a detecting device 9. Detecting device 9 is equipped for detecting first items of information. First items of information are, in general, data that can be processed further by a control unit 10 configured with hardware and/or software accordingly.

Figure 1:
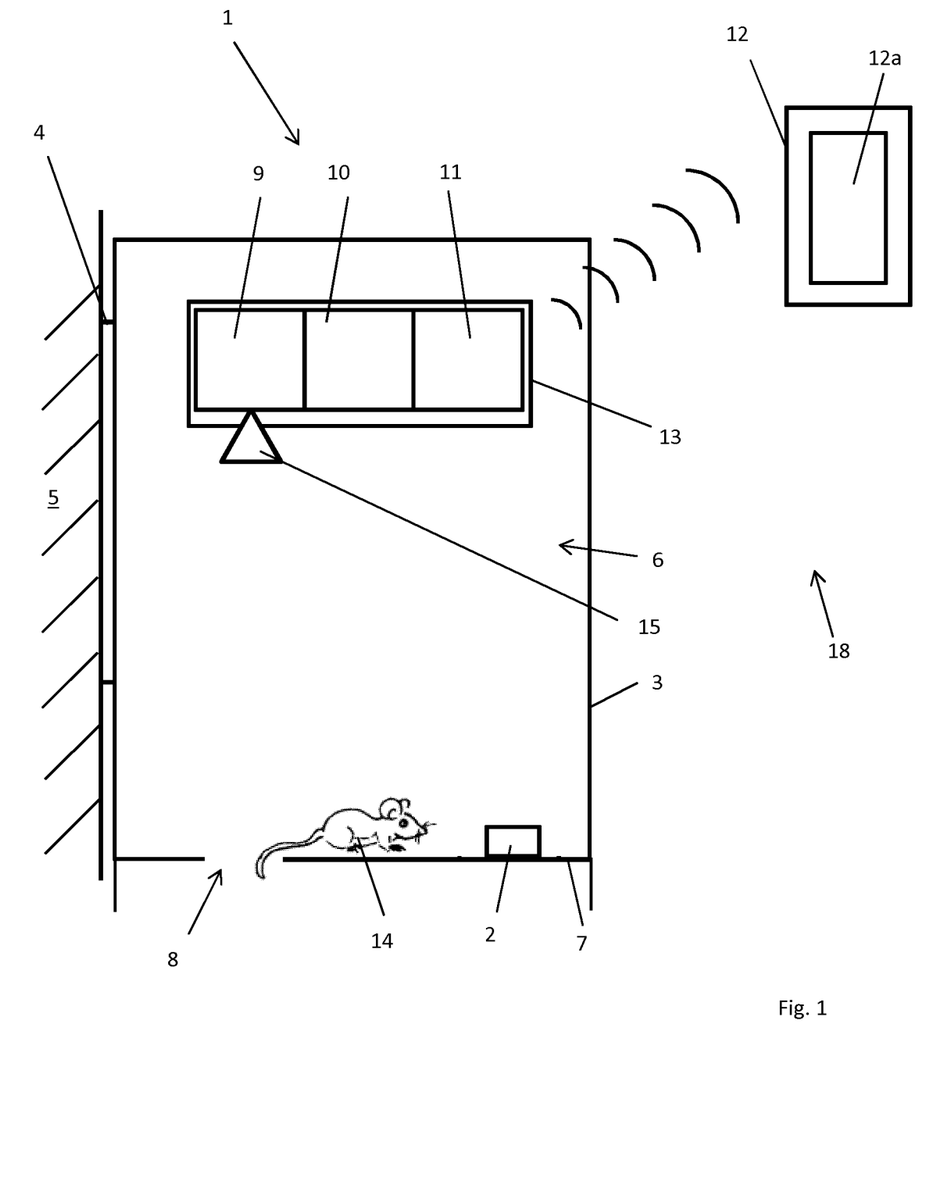
FIG. 1 shows a basic diagram of an apparatus for holding bait according to one exemplary embodiment.
Figure 3:
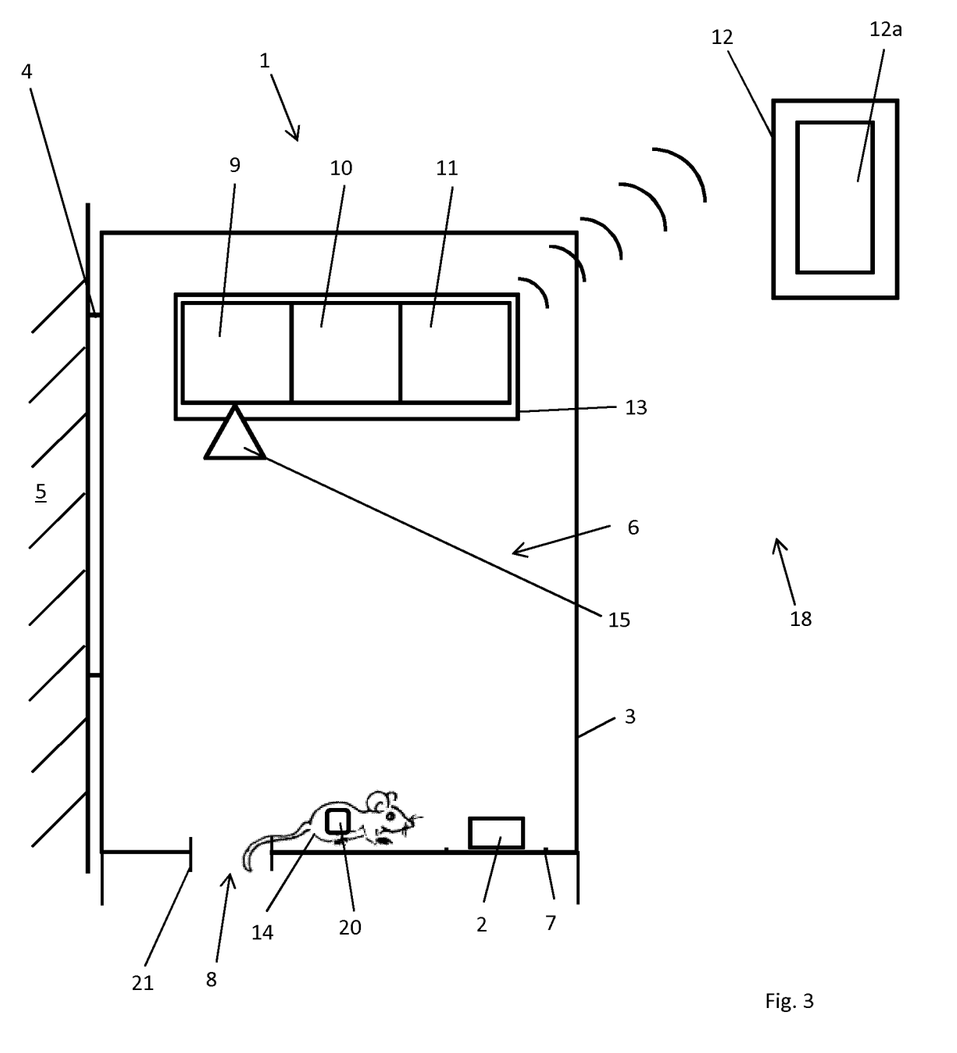
FIG. 3 shows a basic diagram of an apparatus for holding bait according to one exemplary embodiment.
Figure 4:
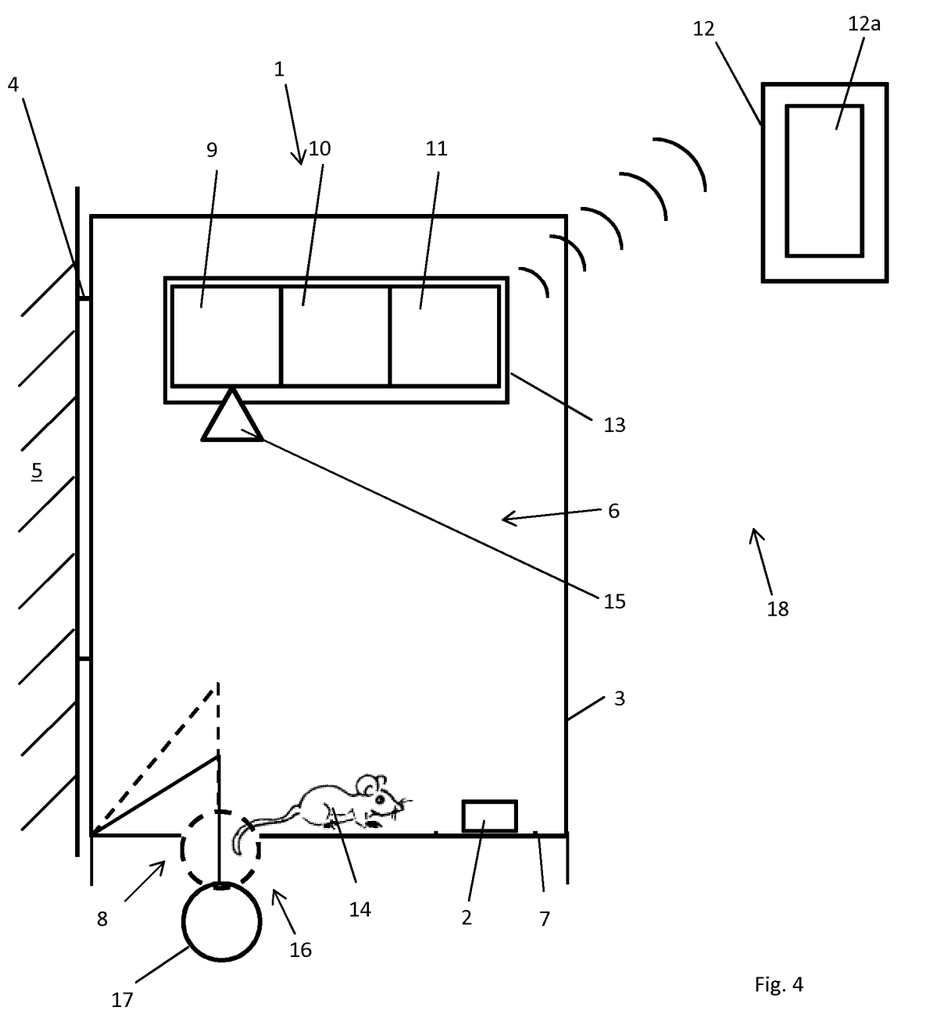
FIG. 4 shows a basic diagram of an apparatus for holding bait according to one exemplary embodiment.

In the exemplary embodiments shown in FIGS. 1, 3 and 4, apparatus 1 additionally comprises a control unit 10. Control unit 10 is connected to and communicates with detecting device 9 via a data link. Control unit 10 is equipped to generate a second item of information on the basis of a first item of information detected by detecting device 9. A second item of information is, in general, data derived from a first item of information by data processing, said data (additionally) being outputtable via an output device 11 configured with hardware and/or software accordingly. The information content of the second item of information differs from the information content of the first item of information due to further data processing. To generate second items of information, control unit 10 is equipped with suitable hardware and/or software elements (not shown); consequently, control unit 10 is configured with hardware and/or software for further processing of data detected by detecting device 9.

Figure 2:
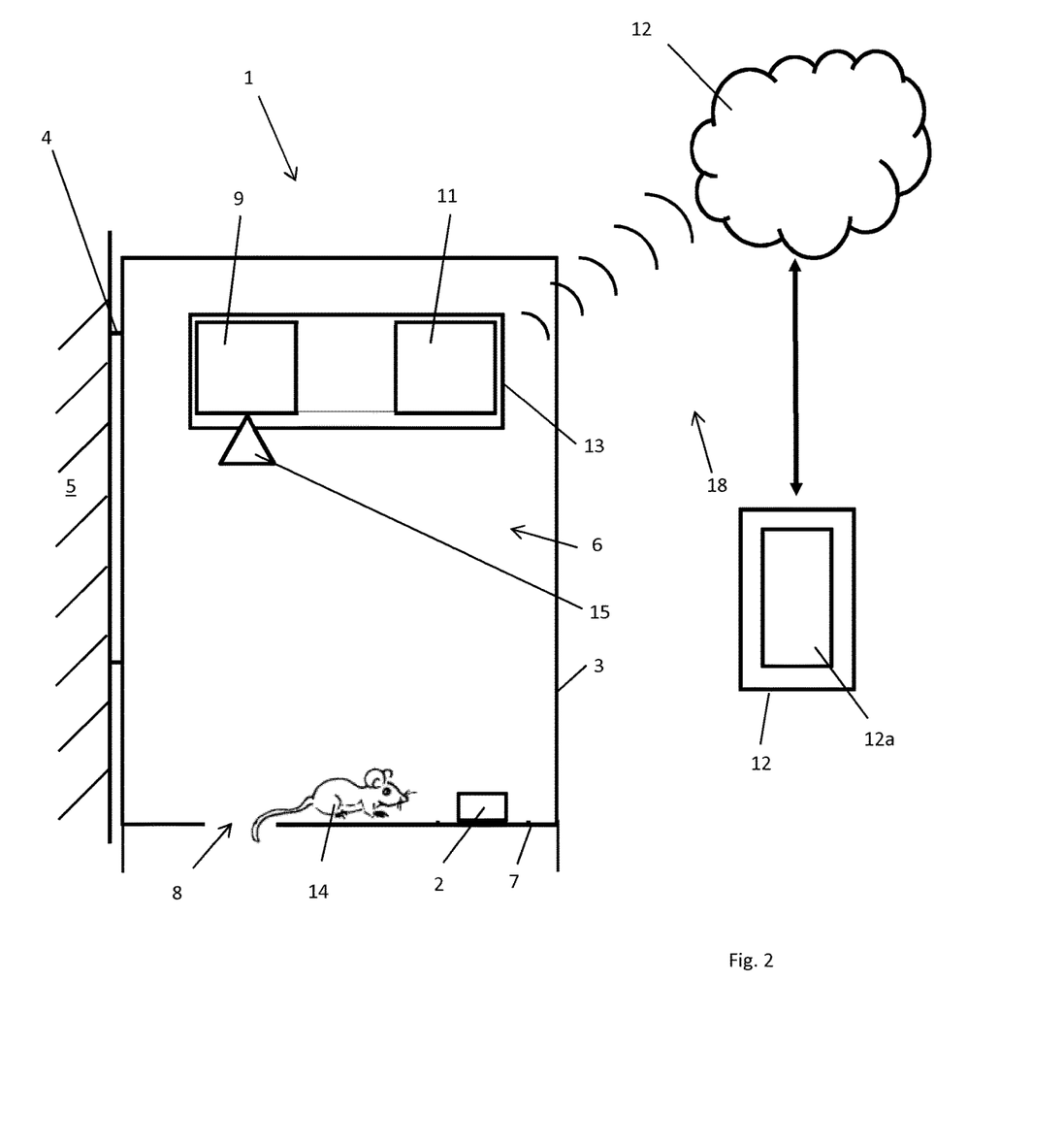
FIG. 2 shows a basic diagram of an apparatus for holding bait according to one exemplary embodiment.

In the exemplary embodiment shown in FIG. 2, apparatus 1 does not comprise a control unit 10; data processing of the first item of information detected by detecting device 9 is not provided on the apparatus end. As also found, data processing of the first items of information detected by detecting device 9 takes place here on the part of a communications partner 12.

In all exemplary embodiments, apparatus 1 comprises an output device 11. Output device 11 is connected to and/or communicates with control unit 10, if present. Output device 11 is equipped for output of first items of information detected by detecting device 9 and/or second items of information generated by control unit 10.

In the exemplary embodiments shown in the figures, output of a first and/or second item of information is understood to mean transmission and/or transfer of the first and/or second items of information to a communications partner 12 communicating with output device 11. Output device 11 is a transmission and/or transfer device equipped accordingly for transmission and/or transfer of first and/or second items of generated information to at least one communications partner 12. In the exemplary embodiments according to FIGS. 1, 3 and 4, communications partner 12 is a (mobile) terminal or operating device at the user end, and in the exemplary embodiment according to FIG. 2, it is a local or global data network, i.e., an Intranet and/or the Internet (cloud), for example. A (mobile) terminal or operating unit at the user end may of course have a data link to the data network.

The first items of information transmitted to the data network, which constitutes communications partner 12, may be processed on data processing equipment communicating with the former (cloud computing). On the part of the data network, there may of course also be further processing of second items of information transmitted to it.

Output device 11 is equipped for radio-based data transmission and/or transfer. Radio-based data transmission is implemented via radio-based data transmission options and/or standards, i.e., Bluetooth, DECT, WLAN, etc., for example. The DECT standard has proven to be particularly reliable for radio-based data transmission from underground mine shaft or sewer systems and is expedient for underground apparatuses 1 to this extent.

Actual and/or direct output of second items of information may be to communications partner 12, wherein the second items of information have been transmitted by output device 11. Communications partner 12 may be equipped with suitable, e.g., acoustic and/or haptic and/or optical, signal output devices 12a, i.e., display and/or loudspeaker devices, for example.

Although not shown in the figures, output device 11 may also be embodied as a signal output device for direct output of signals describing first and/or second items of information to a user. Such a signal output device may be an acoustic signal output device, i.e., a loudspeaker device, for example, an optical signal output device, i.e., a display device, for example, or a haptic signal output device, i.e., a vibration device, for example. Output of a second item of information may thus in principle also be understood to be actual and/or direct output of the second item of information to and/or via output device 11.

Detecting device 9, control unit 10 and output device 11 may each form an integral component of housing part 3. However, it is also conceivable for detecting device 9, control unit 10 and output device 11 to form an integral component of a part 13 that is or can be connected to housing part 3. Part 13 may be a receiving chamber, which is releasably connectable to housing part 3, and in which electrical and/or electronic components of apparatus 1 are arranged, i.e., in particular detecting device 9, control unit 10 and output device 11.

A first item of information may be bait information, which includes and/or describes at least one bait parameter of bait 2. A bait parameter may qualitatively or quantitatively describe, for example, a chemical and/or physical and/or geometric parameter, i.e., the (chemical) composition (chemical parameter), the weight (physical parameter), the shape or volume (geometric parameter) of bait 2.

Alternatively, or additionally, a first item of information may be pest information, which describes and/or includes at least one pest parameter of a pest 14. A pest parameter may qualitatively or quantitatively describe, for example, pests 14 that are detected and/or movements of one or more pests 14 detected inside and/or outside of receiving space 6.

A second item of information may be user information generated on the basis of bait and/or pest information detected. User information may describe and/or include bait dosing information and/or bait checking information and/or pest resistance information.

Bait dosing information may describe and/or include a qualitative and/or quantitative instruction and/or recommendation for introducing (new) bait 2 into receiving space 6, this instruction and/or recommendation being directed at a user and being expedient in particular with regard to a certain target variable, in particular preventing resistances to a certain bait 2 from developing in pest 14. Thus, an instruction and/or recommendation about which bait 2, in particular which active ingredient contained in bait 2 the user should expediently use (in the future) to equip apparatus 1 in order to prevent pest 14 from developing a resistance to a certain type of bait 2, for example. Providing suitable bait dosing information can prevent resistances from developing.

Detected bait information can provide information about the chemical composition of bait 2 held on the apparatus, for example, or about the weight and/or volume of bait 2, which is optionally (un)changed over a certain period of time. Bait dosing information is generated on the basis of an understanding of bait 2 provided by the bait information, i.e., for example, its chemical composition and/or weight and/or volume. Thus, dosing of a different type of bait 2 (if necessary) may be instructed by corresponding bait dosing information.

On the basis of detection and/or with knowledge of the chemical composition of the first bait 2, for example, bait dosing information may instruct the user to dose a second type of bait 2, which is different from the first bait 2 with respect to its chemical composition.

In addition, for example, bait dosing information may instruct the user to dose a second type of bait 2, which has a different chemical composition than bait 2 already dosed, and which will optionally be accepted better by pests 14, and to do so on the basis of detection and/or with knowledge of a weight and/or volume of bait 2, which has shown little or no change over a certain period of time, thus indicating that bait 2 has not been accepted by pests 14.

The bait check information is a qualitative and/or quantitative instruction, directed at a user in particular at a certain point in time or for a certain period of time, to check a given type of bait 2, in particular with regard to changes in bait 2 attributable to the bait having been bitten a pest 14. Thus, an instruction and/or recommendation can be given to a user via corresponding bait check information, indicating when and at which regular or irregular intervals the user should check on a given type of bait 2, in particular with regard to changes in bait 2 to be attributed to a bait bite by a pest 14. Bait check information may basically contain a certain interval of time (checking rhythm) and/or a certain period of time and/or a certain point in time (time of day, day, month, year), within which or at which the user should perform a check of bait 2. The user may also be given check intervals at which the he should perform a check of bait 2.

Pest resistance information may describe and/or include a current and/or future potential for developing a resistance in a pest 14 in comparison with a certain type of bait 2, which may have already been dosed one or more times in the past. Thus, information about resistances (possibly) occurring at the present time and/or in the future can be given to a user via corresponding pest resistance information, so that the user will vary the choice of a type of bait 2 for equipping apparatus 1 accordingly in order to counteract resistances occurring currently and/or in the future. For example, in one case, pest resistance information may indicate a resistance (developed) in pests 14 to a certain type of bait 2, namely bait accommodated in the receiving space 6, based on detection and/or knowledge about an unchanged (increased) number of pests 14 in housing part 3 for a certain period of time.

A detecting element (not shown) equipped for detecting bait information as part of detecting device 9 may be a sensor device for detecting a chemical and/or physical and/or geometric bait parameter. The sensor device may be equipped for detecting certain optionally (readily) volatile substances of bait 2, for example, so that a chemical bait parameter can be detected. In addition, the/an additional sensor device may be equipped for detecting the weight of bait 2, for example, so that a physical bait parameter can be detected. Moreover, the/an additional sensor device may be equipped for detecting the shape and/or volume of bait 2, for example, so that a geometric bait parameter can be detected.

A detecting element may also be a reader for readout of a memory device (not shown) containing a bait parameter, for example, on the bait. The reader is and/or can be connected via data link to a memory device containing a bait parameter, e.g., on the bait, so that the stored bait parameter can be read out. It is thus not absolutely necessary to detect a bait parameter sensorially on the apparatus, and instead a bait parameter can be read out from detecting device 9 and detected in this way.

A detecting element may also be a receiving device for receiving a bait parameter transmitted by a user (before, during or after introduction of bait 2 into receiving space 6). The receiving device, which may form part of output device 11, thus is and/or can be connected via data link to a transmitting device, in particular on the user end, which may form part of a (mobile) terminal and/or operating device on the user end, so that reception of a bait parameter is possible. Therefore, here again, it is not absolutely necessary to detect a bait parameter by sensor on the apparatus end, and instead, a bait parameter may be transmitted to and/or received by detecting device 9 and thereby detected.

A detecting element equipped for detection of pest information may be a sensor device for detecting pests 14 and/or for detecting movements of pests 14 inside and/or outside of receiving space 6. The sensor device may be equipped for detecting an atmosphere and/or a temperature, for example, inside and/or outside of receiving space 6, so that detection of a pest parameter is possible. For example, detection of an atmosphere having a composition (for example, an elevated $CO_2$ content) that has changed in comparison with a reference atmosphere and/or detection of a temperature that has changed in comparison with a reference temperature may indicate the presence of pests 14. The sensor device comprises gas and/or temperature sensors suitable for this purpose. However, the sensor device may also be equipped for detecting forces, in particular compressive and/or tensile forces acting on a surface, i.e., a surface of a wall of housing part 3 and/or a surface of platform device 7, for example, so that detection of a pest parameter is possible. For example, detection of a pressure and/or tension acting on a certain area may indicate the presence of pests 14. The sensor device comprises pressure and/or tension sensors suitable for this purpose.

The figures illustrate a recording device 15, in particular an image and/or sound recording device for recording pests 14 and/or for recording movements of pests 14 inside and/or outside of receiving space 6 as a concrete embodiment of a detecting element equipped for detecting pest information. Recording device 15 may be equipped for recording acoustic and/or optical information inside receiving space 6, so that detection of a pest parameter is possible. For example, recording a certain noise level and/or movement pattern may qualitatively or quantitatively indicate the presence of pests 14. Recording device 15 comprises acoustic and/or optical recording elements, i.e., microphones and cameras, for example, suitable for this purpose.

On the basis of the exemplary embodiment shown in FIG. 3, it can be seen that a detecting element equipped for detecting pest information may also be a sensor device for detecting a marker device 20 (marker) on the pest, i.e., externally or internally associated with a pest, in particular a biological, chemical, magnetic or mechanical marker. The sensor device may thus detect certain marker devices 20 on the pest, which supply information about the presence and/or movement pattern of pests 14 associated therewith. Biological and/or chemical marker devices 20 may be certain biological or chemical substances, which have been dosed to a pest 14 externally or internally. For example, the surface of a pest 14 may be wetted with a corresponding substance. Magnetic or mechanical marker devices 20 may be magnetic or mechanical elements, which are detectable magnetically or mechanically, for example, i.e., by mechanical contact, and which can be administered to a pest 14 externally or internally. For example, a corresponding element may be attached to a body part of a pest 14.

For marking a pest 14 with a marker device 20, apparatus 1 may comprise a marking device 21. Marking device 21 is equipped for marking a pest 14 with a biological, chemical, magnetic or mechanical marker device 20, which is detectable by the sensor device belonging to detecting device 9 for detecting a marker device 20 on the pest. Marker device 20 may be employed, for example, by spraying, contacting a contact region provided with a marker device 20, for example, a brush-type contact region, or by spraying, binding, gluing, stapling, etc.—depending on the structural aspects thereof. In the exemplary embodiment shown in FIG. 3, a marking device 21 is arranged or formed in the area of passage 8 in platform device 7. Marking device 21 thus forms a part of housing part 3.

In principle, a marking device 21 arranged or formed outside of housing part 3 and/or apparatus 1 may also be provided.

A detecting element equipped for detecting pest information may also be a reader for readout of a memory device (not shown) (memory chip, tag, etc.) containing a pest parameter, in particular on the pest. The reader is and/or can be connected via data link to a pest 14 and/or to a memory device containing a pest parameter, so that readout of the pest parameter is possible. Readout is possible, for example, when a pest 14 is inside a reading area. Such a reading area may be located inside or outside of housing part 3.

Apparatus 1 may also comprise a memory device (not shown). The memory device is equipped for storing first items of information detected by detecting device 9, i.e., in particular bait information and/or pest information, and/or for storing second items of information generated by control unit 10, i.e., in particular user information, in particular bait dosing information and pest resistance information.

It can be seen on the basis of the exemplary embodiment shown in FIG. 4 that apparatus 1 may comprise a closing device 16. Closing device 16 comprises a closing body 17 that is movably mounted on housing part 3, so that it is movable relative to the latter between an open position and a closed position. In the open position (represented by a solid bar in FIG. 3), closing body 17 is moved away from the access region of housing part 3 into receiving space 6, i.e., passage 8, so that the access region is opened. In the closed position (represented by a dashed line in FIG. 3), closing body 17 is moved toward the access region, so that the access region is sealed, in particular hermetically. In the closed position, contamination with substances contained in bait 2 is prevented. Closing body 17 may thus be a float, which moves on its own into the closed position when the water level rises.

With apparatus 1, shown in the figures, a transmission system 18 may be implemented for transmitting information, in particular user information, preferably bait dosing information and/or pest resistance information, to at least one communications partner 12. Transmission system 18 comprises at least one apparatus 1 as well as at least one communications partner 12, which is equipped at least to receive second items of information transmitted from output device 11 on the apparatus end. Communications partner 12 may be a terminal and/or operating device (mobile) on the user end, i.e., in particular a laptop, smartphone, tablet PC or other mobile electronic device.

A method for transmitting information, in particular user information, preferably bait dosing information and/or pest resistance information, to at least one transmission and/or communications partner 12 can be implemented with transmission system 18.

In a first embodiment, the method comprises the following steps:
  detecting a first item of information, in particular bait information, describing at least one bait parameter of bait 2, and/or pest information, describing at least one pest parameter of a pest 14, by detecting device 9 of apparatus 1, and
  transmitting the first item of detected information to at least one transmission partner 12 by output device 11 of apparatus 1.

Data processing of the first items of information may take place here outside of apparatus 1.

This method comprises the following steps of a second embodiment:
  detecting a first item of information, in particular bait information, describing at least one bait parameter of bait 2, and/or a pest information, describing at least one pest parameter of a pest 14, by detecting device 9 of apparatus 1,
  generating a second item of information, in particular user information, on the basis of a first item of information detected, in particular bait information and/or pest information detected, by means of control unit 10 of apparatus 1, and
  transmitting the second item of information generated to at least one transmission partner 12 by output device 11 of apparatus 1.

Data processing of the first item of information may (also) take place here in apparatus 1.

The invention claimed is:
1. An apparatus for holding bait, in particular bait for pests, preferably rodents, comprising:
  a housing part that can be inserted into a part of a sewer system in particular, having a receiving space for receiving a piece of bait,
  a detecting device equipped for detecting a first item of information, wherein the first item of information is bait information, describing at least one bait parameter of bait, and/or pest information, describing at least one pest parameter of a pest, a control unit equipped to generate a second item of information on the basis of the first item of information detected by detecting device, wherein the output device is equipped for output of the second item of information generated by the control unit, the second item of information comprising user information generated on the basis of bait information detected and/or pest information detected, wherein the user information is bait dosing information and/or bait check information and/or pest resistance information, and an output device equipped for output of the first item of information detected by the detecting device, wherein the bait dosing information describes a qualitative and/or quantitative instruction that is directed at a user and is expedient in particular with regard to a certain target variable.

2. The apparatus according to claim 1, characterized in that the bait parameter describes qualitatively or quantitatively at least one chemical and/or physical and/or geometric parameter of bait accommodated in the receiving space on the housing part and/or qualitatively or quantitatively describes at least one parameter derived from a chemical and/or physical and/or geometric parameter of bait accommodated in the receiving space on the housing part.

3. The apparatus according to claim 1, characterized in that the pest parameter describes qualitatively or quantitatively the pests and/or movements of one or more pests detected inside and/or outside of the receiving space in/on the housing part and/or qualitatively or quantitatively describes at least one parameter derived from detected pests and/or from movements of one or more detected pests inside and/or outside of the receiving space in/on the housing part.

4. The apparatus according to claim 1, characterized in that the detecting device comprises at least one detecting element for detecting the bait parameter and/or the pest parameter.

5. The apparatus according to claim 4, characterized in that a detecting element is designed for detecting a bait parameter
- as a sensor device for detection of a chemical and/or physical and/or geometric bait parameter or
- as a reader for readout of a memory device containing a bait parameter, in particular on the bait or
- as a receiving device for receiving a bait parameter, in particular transmitted by a user.

6. The apparatus according to claim 1, characterized in that a detecting element for detecting a pest parameter is designed as a sensor device for detecting pests and/or movements of one or more pests inside and/or outside of the receiving space on the housing part or as a sensor device for detecting a biological, chemical, magnetic or mechanical marking device, in particular on the pest, or as a reader for readout of a memory device containing a pest parameter, in particular a memory device on the pest, or as a recording device, in particular an acoustic and/or optical recording device, for recording pests and/or movements of one or more detected pests inside and/or outside of the receiving space on the housing part.

7. The apparatus according to claim 1, characterized by a memory device equipped for storing a first item of information detected by the detecting device and/or for storing second items of information generated by the control unit.

8. The apparatus according to claim 1, characterized in that the output device is designed as a signal output device for direct output of signals describing second items of generated information to at least one user, or the output device is designed as a transmitting device equipped for transmission, in particular radio-based, of first items of information detected by the detecting device and/or second items of information generated by the control unit to at least one transmission partner, in particular to a terminal and/or operating device on the user end and/or to a local or global data network.

9. The apparatus according to claim 1, characterized in that the detecting device and/or the control unit and/or the output device and/or the marking device form(s) an integral component of the housing part, or the detecting device and/or the control unit and/or the output device and/or the marking device form(s) an integral component of a separate component that is or may optionally be connected to the housing part or is separate from the housing part.

10. The apparatus according to claim 1, characterized by a closing device, which comprises a closing body, mounted on the housing part in particular, movable relative to the housing part between an open position and a closed position, wherein the closing body, when in the open position, is moved away from an access region into the receiving space on the housing part, such that the access region is opened, and when in a closed position, is moved toward the access region, such that the access region is sealed, in particular hermetically.

11. An apparatus for holding bait, in particular bait for pests, preferably rodents, comprising:
- a housing part that can be inserted into a part of a sewer system in particular, having a receiving space for receiving a piece of bait,
- a detecting device equipped for detecting a first item of information, wherein the first item of information is bait information, describing at least one bait parameter of bait and/or pest information, describing at least one pest parameter of a pest,
- a control unit equipped to generate a second item of information on the basis of the first item of information detected by detecting device, wherein the output device is equipped for output of a second item of information generated by the control unit, the second item of information comprising user information generated on the basis of bait information detected and/or pest information detected, wherein the user information is bait dosing information and/or bait check information and/or pest resistance information, and
- the bait check information describes a qualitative and/or quantitative instruction, which is directed at a user at a certain point in time or within a certain period of time, for checking a given bait that can be attributed to a pest having taken a bite of the bait.

12. An apparatus for holding bait, in particular bait for pests, preferably rodents, comprising:
- a housing part that can be inserted into a part of a sewer system in particular, having a receiving space for receiving a piece of bait,
- a detecting device equipped for detecting a first item of information, wherein the first item of information is bait information, describing at least one bait parameter of bait and/or pest information, describing at least one pest parameter of a pest,
- a control unit equipped to generate a second item of information on the basis of the first item of information detected by detecting device, wherein the output device is equipped for output of a second item of information generated by the control unit, the second item of information comprising user information generated on the basis of bait information detected and/or pest information detected, wherein the user information is bait dosing information and/or bait check information and/or pest resistance information, and an output device equipped for output of the first item of information detected by the detecting device, wherein the pest resistance information describes a present and/or future potential for a pest to develop resistance to a certain type of bait, optionally already dosed one or more times in the past.

13. An apparatus for holding bait, in particular bait for pests, preferably rodents, comprising:
  a housing part that can be inserted into a part of a sewer system in particular, having a receiving space for receiving a piece of bait,
  a detecting device equipped for detecting a first item of information,
  an output device equipped for output of a first item of information detected by, the detecting device, further comprising a marking device equipped for marking a pest with a marker device, in particular a biological, chemical, magnetic or mechanical marker device detectable by the sensor device for detection of a marker device on the pest.

14. A transmission system for transmitting information to at least one transmission partner, comprising:
  at least one apparatus for holding a piece of bait according to claim 1,
  at least one transmission partner, equipped at least for receiving second items of information transmitted via the output device on the apparatus end.

15. A method for transmitting information to at least one transmission partner characterized by the following steps:
  detecting a first item of information, in particular bait information, describing at least one bait parameter of a piece of bait and/or a pest information, describing at least one pest parameter of a pest, by a detecting device of an apparatus for holding bait according to claim 1, and
  transmitting the first item of information detected to at least one transmission partner by means of an output device of the apparatus for holding bait, or
  detecting a first item of information, in particular bait information, describing at least one bait parameter of a piece of bait and/or pest information, describing at least one pest parameter of a pest, by the detecting device of the apparatus for holding bait,
  generating a second item of information, in particular user information, on the basis of the first item of detected information, in particular bait information and/or detected pest information, by the control unit of the apparatus for holding bait, and
  transmitting the second item of information generated to at least one transmission partner by the output device of the apparatus for holding bait;
  wherein the bait dosing information describes a qualitative and/or quantitative instruction that is directed at a user and is expedient in particular with regard to a certain target variable.

* * * * *